United States Patent
Williamson (10) Patent No.: US 8,226,969 B2
(45) Date of Patent: Jul. 24, 2012

(54) METHODS FOR REDUCING THE INCIDENCE OF MASTITIS

(75) Inventor: Norman Bruce Williamson, Palmerston North (NZ)

(73) Assignee: Massey University, Palmerston North (NZ)

(*) Notice: Subject to any disclaimer, the term of this patent is extended or adjusted under 35 U.S.C. 154(b) by 282 days.

(21) Appl. No.: 12/377,967

(22) PCT Filed: Aug. 17, 2007

(86) PCT No.: PCT/NZ2007/000219
§ 371 (c)(1), (2), (4) Date: Dec. 17, 2009

(87) PCT Pub. No.: WO2008/020769
PCT Pub. Date: Feb. 21, 2008

(65) Prior Publication Data
US 2010/0166807 A1    Jul. 1, 2010

(30) Foreign Application Priority Data
Aug. 18, 2006   (NZ) ........................................ 549249

(51) Int. Cl.
*A61K 9/00*    (2006.01)
*A61F 13/00*   (2006.01)
*A23K 1/18*    (2006.01)
(52) U.S. Cl. ..................... 424/422; 424/438; 424/400
(58) Field of Classification Search .................. None
See application file for complete search history.

(56) References Cited

U.S. PATENT DOCUMENTS

| 7,066,995 B1 | 6/2006 | Barone et al. |
| 2003/0228353 A1 | 12/2003 | Cowsar |
| 2005/0191270 A1* | 9/2005 | Gruening et al. ............ 424/78.3 |
| 2005/0271694 A1* | 12/2005 | Mansouri et al. ............ 424/423 |

FOREIGN PATENT DOCUMENTS

| WO | WO-98/48627 | 11/1998 |
| WO | WO-2005/027775 | 3/2005 |

OTHER PUBLICATIONS

M.W. Woolford, et al., "The Prophylactic Effect of a Teat Sealer on Bovine Mastitis During the Dry Period and the Following Lactation", New Zealand Veterinary Journal 46, 12-19, 1998, pp. 12-18.
S.C. Nickerson, Phd, Review Article, "Resistance Mechanisms of the Bovine Udder: New Implications for Mastitis Control At the Teat End", JAVMA, vol. 191, No. 11, Dec. 1, 1987, Supplied by the British Library—"The World's Knowledge". pp. 1484-1487.
Fiona Crispie, et al., "Dry Cow Therapy With a Non-Antibiotic Intramammary Teat Seal—A Review", Irish Veterinary Journal, vol. 57, pp. 412-418, Jul. 2004.

* cited by examiner

*Primary Examiner* — Carlos Azpuru
*Assistant Examiner* — Casey Hagopian
(74) *Attorney, Agent, or Firm* — Connolly Bove Lodge & Hutz LLP (57) ABSTRACT

The invention encompasses methods of reducing the incidence of mastitis in an animal, and compositions and devices therefor. The methods and other aspects of the invention can be used to reduce the incidence of infection in the teat or mammary gland. In particular, but not exclusively, the invention encompasses a method of applying to the teat canal and/or teat sinus a composition comprising exogenous keratin.

10 Claims, 2 Drawing Sheets

METHODS FOR REDUCING THE INCIDENCE OF MASTITIS

CROSS REFERENCE TO RELATED APPLICATIONS

This application is a National Stage of PCT/NZ2007/000219 filed Aug. 17, 2007 which in turn claims priority from New Zealand Application 549249 filed Aug. 18, 2006, the entire contents of which are incorporated herein by reference.

RELATED APPLICATION

This application claims the benefit of New Zealand Provisional Patent Application 549249 filed 18 Aug. 2006, which is incorporated herein by reference in its entirety.

FIELD OF INVENTION

The invention relates to methods of reducing the incidence of mastitis in an animal, including a reduction in infection, and compositions and devices therefor. In particular, but not exclusively, the invention relates to a method of applying to the teat canal and/or teat sinus a composition comprising exogenous keratin.

BACKGROUND

Mastitis is an inflammation of the mammary gland that is caused by bacteria which in most cases enter the gland via the teat orifice. Deposits of keratin in the teat orifice and the streak canal form a primary defence mechanism. Keratin contains high levels of naturally occurring anti-bacterial substances which inhibit the passage of bacteria from the teat orifice to the cistern (papillary sinus).

The defensive plug of keratin that accumulates in the streak canal is dislodged during milking. Furthermore, the keratin plug has increased mass in dry cows than lactating cows. Susceptibility to mastitis is exacerbated by regular milking, particularly by mechanical milking processes that result in damage to the tissues of the teat in the vicinity of the teat orifice. If the keratin plug does not reform properly after milking ceases at drying off, a cow is much more likely to develop mastitis during the non-lactation period and when milking recommences.

International application number PCT/NZ2004/000231 (Publication No. WO 2005/027775) describes a device to promote the deposition and retention of endogenous keratin within the teat canal. In addition, the device may be made of a preformed matrix such as silicone which is able to deliver treatment substances. The device is contrasted with low viscosity pastes and gels that are not able to provide precise positioning of substance for control over the volume of composition infused.

The device is retained in the teat orifice and is required to be removed prior to milking. This requirement introduces an additional step in the manually intensive procedure of milking cows.

International application number PCT/SE98/00776 (Publication No. WO 98/48627) describes a teat dipping solution for lactating cows. The teat dipping solution is used prophylactically or as a wound healing treatment against mastitis. The teat dipping solution comprises chitosan in combination with a polysaccharide selected from heparin, heparin sulphate, and dextran sulphate.

The composition described is an alternative to other veterinary compositions for reducing mastitis such as those described in U.S. Pat. No. 4,472,374. These latter compositions are introduced directly into the teat canal. During the introduction of these compositions into the teat canal endogenous keratin that may have been deposited is dislodged, thereby diminishing the natural defence to infection. Furthermore the use of these compositions may place restrictions on when the milk collected from treated cows, may enter the human food chain.

The trade name products TEATSEAL and ORBESEAL are anti-microbial compositions. These products comprise bismuth subnitrate in an oily base. The composition is supplied in an injector for infusing the composition into the teat to form a seal. Milk collected from animals within three days of this treatment and intended for human consumption must be discarded. Accordingly, there is a commercial disadvantage to farmers if milk or colostrum collected from treated cows cannot be sold.

An object of the present invention is to overcome one or more of the disadvantages of the prior art, or at least to provide the public with a useful choice.

SUMMARY OF THE INVENTION

In a first aspect, the invention broadly encompasses a method for reducing the incidence of mastitis in an animal including the step of: introducing a composition comprising keratin into the teat canal of the animal. Typically, the method is employed in a recently dried off animal or during the non-lactating period of the animal. Preferably, the animal is a cow.

In a first alternative, the composition is in a form suitable for introduction by means of a device, e.g., a syringe. Preferably, the composition is in the form of a paste. Most preferably, the composition has a viscosity of between $0.1 \times 10^6$ cP and $1.5 \times 10^6$ cP.

In a second alternative, the composition is in a form suitable for introduction by hand. Preferably, the composition is in the form of a wax-like solid. Most preferably, the composition is pre-formed into a stick or peg shape.

In a second aspect, the invention broadly encompasses a composition comprising keratin formulated for introduction into the teat canal of an animal. Preferably, the animal is a cow.

In a first embodiment, the composition is a paste. Preferably the composition has a viscosity of between $0.1 \times 10^6$ cP and $1.5 \times 10^6$ cP.

In a second embodiment, the composition is a wax-like solid. Preferably, the composition is pre-formed into a stick or peg shape.

Preferably, the composition comprises keratin compounded in a milk derived medium. Preferably, the composition comprises keratin compounded in an aqueous medium. Preferably, the composition comprises keratin dispersed in a food grade lipid medium. More preferably, the food grade lipid is a fatty acid or glyceride. Most preferably, the food grade lipid is stearate.

Optionally, the composition additionally comprises one or more exogenously provided antibacterial substances, where the substances are selected from the group consisting of: fatty acids and lactoferrin.

In a third aspect, the invention broadly encompasses an apparatus adapted for introducing a composition comprising keratin into the teat canal of an animal. Preferably, the keratin is physically processed to provide a composition comprising the physically processed keratin with a viscosity of between $0.1 \times 10^6$ cP and $1.5 \times 10^6$ cP. Preferably, the apparatus is a syringe.

In a fourth aspect, the invention broadly encompasses a method for inducing leucocytosis, e.g., short term leucocytosis, in the mammary gland of an animal including the step of: introducing a composition comprising keratin into the teat canal of the animal. Preferably, the composition is in a form as described herein above.

In a specific embodiment, the method stimulates short-term leucocytosis, followed by resolution, to aid in protecting the udder from bacterial infection. Typically the method is employed in a recently dried off animal or during the non-lactating period of the animal. Preferably the animal is a cow.

The invention will now be described in detail with reference to the figures of the accompanying drawings and one or more non-limiting examples.

DETAILED DESCRIPTION

The inventor has recognised the advantage of providing a composition for introduction into the teat canal of cows that does not require a withholding period for milk collected from treated cows subsequent to calving. The use of physical processing of keratin to provide a composition devoid of chemical modification or by-products that could result in a withholding period being established is particularly advantageous.

In a preferred embodiment of the invention a composition for introduction into the teat canal of an animal is provided, where the composition comprises solely exogenously prepared and physically processed keratin and food grade substances. The advantages of the invention will be most readily be realised when the method is employed during the non-lactating period of animals used in the production of milk and other dairy products for human consumption. In alternative embodiments, the animal is a milk producing animal, e.g., dairy animal, selected from the group consisting of cows, goats, sheep, buffalos, and yaks.

The keratin is processed to provide a composition with a viscosity that permits facile introduction into the teat canal, yet does not result in a composition that is readily expelled from the teat canal as milk pressure immediately following the cessation of milking builds up. In various embodiments, the viscosity in the range of about $0.1 \times 10^6$ cP to about $1.5 \times 10^6$ cP. In other embodiments, the viscosity is in the range of about $0.5 \times 10^6$ cP to about $1.0 \times 10^6$ cP; about $0.75 \times 10^6$ cP to about $1.25 \times 10^6$ cP; $0.7 \times 10^6$ cP to about $0.9 \times 10^6$ cP. In further embodiments, the viscosity is about $0.1 \times 10^6$ cP, about $0.2 \times 10^6$ cP, about $0.3 \times 10^6$ cP, about $0.4 \times 10^6$ cP, about $0.5 \times 10^6$ cP, about $0.6 \times 10^6$ cP, about $0.7 \times 10^6$ cP, about $0.8 \times 10^6$ cP, about $0.9 \times 10^6$ cP, about $1.0 \times 10^6$ cP, about $1.1 \times 10^6$ cP, about $1.2 \times 10^6$ cP, about $1.3 \times 10^6$ cP, about $1.4 \times 10^6$ cP, or about $1.5 \times 10^6$ cP.

Optionally, the composition additionally comprises one or more exogenously provided antibacterial substances, for example, where the substances are selected from the group consisting of: fucosylated oligosaccharides, glycoproteins such as lactoferrin and lactadherin, fatty acids, e.g., free fatty acids, long-chain unsaturated fatty acids and medium-chain saturated fatty acids, and lysozyme. While it is preferable to avoid antibiotic treatment where possible, the composition can also be used in conjunction with one or more antibiotic agents, for example, cephapirin (e.g., CEFA-LAK 7) and oxytetracycline, and one or more anti-inflammatory therapies such as oxytocin and flunixin meglumine (e.g., BANAMINE 7).

The composition can also include one or more physiologically acceptable constituents, such as diluents, carriers, and/or excipients, and/or one or more stabilizers, thickeners, fillers, emulsifiers, coatings, lubricants, binders, buffers, surfactants, plasticizers, colorants, preservatives (e.g., antimicrobial agents), dosing vehicles, or any combination thereof. In particular aspects, the composition is provided in sterile form for insertion. For example, the composition can be sterilized by gamma, X-ray, or electron-beam irradiation, or radioisotope source irradiation, e.g., by cobalt-60.

The composition can be inserted by hand or by use of an apparatus. Devices suitable for the introduction of the composition of the invention into the teat canal are known to those skilled in the art. For example, international application number PCT/US02/07100 (Publication No. WO 02/070057) describes an applicator for administering a medication made up of an elongated syringe having an integral blunt-tipped cannula provided at one end. The introduction of a pre-determined amount of the composition into the teat canal following the last milking before drying off provides the additional advantage that the natural defences of the cow to mastitis are augmented. The deposition of endogenous keratin combines with and further enhances the barrier protection provided by the introduction of the exogenously prepared keratin.

The compositions and methods of the invention can be used to reduce the incidence of infection (e.g., bacterial infection). In a preferred embodiment, the invention encompasses a method for reducing the incidence of mastitis in an animal. The invention further encompasses a method for inducing leucocytosis in an animal. In specific aspects, the method can be used to stimulate short-term leucocytosis to aid in protecting the udder from bacterial infection during the period after drying off. This would be the most susceptible period for infection. As used herein, "reducing" (e.g., reducing incidence of infection) can include preventing, curing, or ameliorating the infection, or reducing at least a symptom of such infection. In particular, this includes preventing or delaying the onset of the infection; curing, correcting, decreasing, slowing, or ameliorating the physical effects of the infection; and/or preventing, ending, diminishing, or ameliorating the pain or suffering caused the infection.

The following non-limiting examples describe proposed compositions and the method of the invention.

EXAMPLES

The examples described herein are for purposes of illustrating embodiments of the invention. Other embodiments, methods, and types of analyses are within the scope of persons of ordinary skill in the art and need not be described in detail hereon. Other embodiments within the scope of the art are considered to be part of this invention.

Example 1

Figure 1:
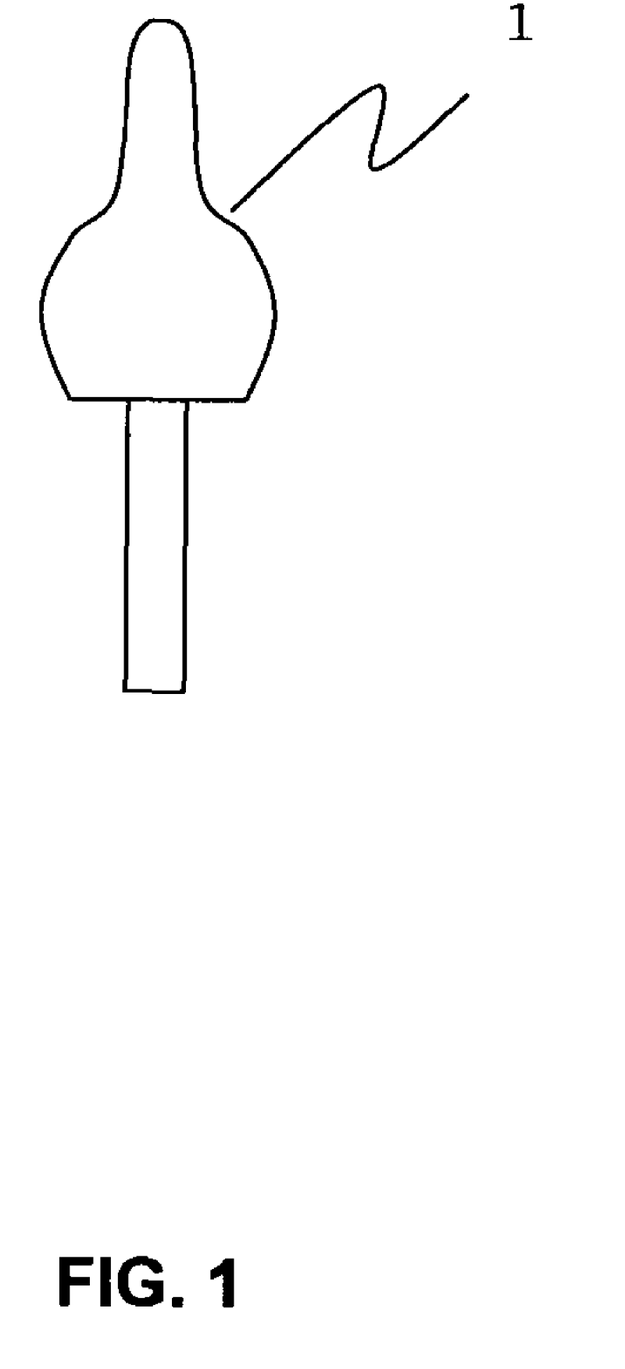
FIG. 1. The shape of a composition in accordance with the second embodiment of the second aspect of the invention that would allow easy insertion into the teat canal.

The composition is keratin in either an aqueous or lipid medium. When in the form of an ointment or gel the composition has a viscosity in the range of $0.1 \times 10^6$ cP to $1.5 \times 10^6$ cP. The composition is introduced into the teat canal using a syringe with an appropriate nozzle (e.g. nozzles used for dry cow treatment which have a collar to prevent over insertion). When in the form of a solid or semi-solid the composition is moulded into a peg or pin which could be inserted manually. A shape (1) that would allow easy insertion into the teat canal is illustrated in FIG. 1.

The composition is introduced immediately after the last milking before drying off (non-lactation period). Each quarter is hand stripped prior to first milking to remove any residual material. It is possible that the plug may be naturally expelled prior to this by the secretion and passage of endogenous keratin. Advantageously, a composition comprising solely keratin, or keratin and food grade substances, will not be subject to a withholding period for milk or colostrum intended for human consumption. The inventor has recognised the importance of this as the value of colostrum products, for example, increases.

Example 2

Keratin Teat Seal Study

Supplies of processed keratin having suitable consistency for intramammary infusion were obtained. Product was used in testing, initially in vitro and then in vivo. Initial tests were conducted to determine the ability of the formulation to maintain its physical form in the likely environment of the teats of cows.

Observations on a Keratin Based Teat Sealant in Milk and Water

The objective of the study included the goal of making observations as to the stability of the keratin-based teat sealant when immersed in vitro in two different environments—water and milk.

Test Material

The test material arrived packaged as a 2 ml syringe, with an attachment for infusion that had a smaller than desired aperture. It was reported that test material had been exposed to gamma irradiation, but potentially non-sterile.

Study Procedures

Approximately 0.5 ml of the test product was squeezed into two 60 ml sterile containers and approximately 35 ml of milk or water was added to each container. The containers were stored in the door of a kitchen fridge in a cardboard box, and visually observed once a day for macroscopic changes to the test product.

At observation the cardboard box was removed from the fridge for approximately 5 minutes and containers removed. Each container was opened and the milk was decanted, visual observation made, and the milk returned to the container. The lid of the water container was removed, observations made and the lid replaced.

Observations were recorded daily as follows, immediately after returning the box to a refrigerator.

Schedule of Events

| Day | Event |
| --- | --- |
| Day 1 | Test product squeezed in container and water or milk added |
| Day 2-6 | Observed and observations recorded |

Results

| Day | Time | Water container | Milk container |
| --- | --- | --- | --- |
| 2 | 14.45 | slightly swollen, no disintegration | no observed changes |
| 3 | 7.40 | very swollen (~3 times apparent volume), no disintegration detected, A more granular visual appearance to substance | no visible swelling, possible surface disintegration, as there is a glossy appearance to the surface |
| 4 | 9.25 | further swelling (~4-5 times the day 1 volume), other changes as for day 3 | no visible changes from day 3 |
| 5 | 8.35 | no visible changes from day 4 | slightly more disintegration on the surface; no other changes from day 4 |
| 6 | 8.05 | no visible changes from day 5 | no visible changes from day 5 |

Conclusion

Keratin appeared to be highly susceptible to the difference in osmolarity in the environments. It is unlikely that a hypotonic environment will be present in the teat at any time over the dry period. It is more likely that there will be a hypertonic environment.

Additionally, it is possible that surface exposure to components in milk cause a slight disintegration of the keratin-based teat sealant. If so, this type of exposure is more likely to occur during the dry period, during involution and colostrogenesis when the dry cow secretions are more like milk. From this, it was concluded that the observations should be repeated with more quantitative approach and to include normal saline as a medium to allow a simple investigation of the impact of osmolarity.

Example 3

In Vitro Observations on a Proposed Keratin-Based Teat Sealant in Milk, Distilled Water and Saline to Determine Effects of Different Osmolarity The objective of the study included the goal of obtaining observations the stability of the keratin-based teat sealant when immersed in vitro in distilled water, saline, and milk.

Test Material

The test material arrived packaged as a 2 ml syringe, with an attachment for infusion that had a smaller than desired aperture. It was reported that test material had been exposed to gamma irradiation, but potentially non-sterile. Half of the received material was used for preliminary observations, as described in the previous example.

Study Procedures

Small amounts of the test product (approximately 0.3 ml each) were squeezed into three 30 ml sterile containers and approximately 12 ml of distilled water, saline or milk was added to one of the containers. Each container was weighed on three occasions: empty, after the keratin-based teat sealant was added and after adding the treatment fluid. The containers were stored at room temperature in a styrofoam box, and visually observed once daily for macroscopic changes to the test product.

At observation, the containers were removed from the styrofoam box for approximately 5 minutes. The container holding the test substance was examined and (if required), inverted to allow measurement and recording of the dimensions of the test material. After observations, each container was returned to the styrofoam box. Findings were recorded at each observation. Weights were taken and recorded at the trial's end (observation 6). Each container was weighed before opening and after the fluids were decanted. Some residual fluids were present, in particular in the container that contained distilled water. Photographs of the test material in different media were taken when possible.

Schedule of Events

| Observation | Event |
|---|---|
| Day 0 | Test product squeezed into container and then distilled water, saline, or milk added. Weights, widths, and heights measured and recorded. |
| Day 1-3 | Twice daily measurement and observations recorded |
| Day 3 | Study ended after observation and recording of weights, widths and heights |

Results

TABLE 1

Measurements at the beginning of the trial

| Media | empty container | +KBTS[1a] | +media[2a] | Width[b] | Height[b] |
|---|---|---|---|---|---|
| Milk | 7.8353 | 8.0492 | 19.6820 | 8 | 10 |
| Distilled water | 7.8924 | 8.2042 | 19.0382 | 16 | 12 |
| Saline | 7.5993 | 7.8620 | 19.7719 | 13 | 11 |

[a] in grams;
[b] in millimetres;
[1] Container weight after adding keratin-based teat sealant;
[2] Container weight after adding keratin-based teat sealant and media Measurements and visual observations at each examination are presented for each medium in Tables 2-4.

TABLE 2

Records for each observation for the keratin-based teat sealant in milk

| Exm[1] | Time | Visual changes | Width | Ch-width[2] | Height | Ch_Height[3] |
|---|---|---|---|---|---|---|
| 1 | 16 hrs | Surface appears shiny | 8 | 0 | 11 | 1 |
| 2 | 24 hrs | NOC[4] | 7 | −1 | 11 | 0 |
| 3 | 40 hrs | NOC | 7 | 0 | 11 | 0 |
| 4 | 48 hrs | NOC | 7 | 0 | 11 | 0 |
| 5 | 64 hrs | NOC | 6.5 | −0.5 | 11 | 0 |
| 6 | 72 hrs | NOC | 6.5 | 0 | 11 | 0 |
| TOTAL | | | 8 | −1.5 | 10 | 1 |

[1] Examination number;
[2] Change in the width from the previous observation (=previous observation − present observation);
[3] Change in the height from the previous observation (=previous observation − present observation);
[4] No obvious changes

TABLE 3

Records for each observation for the keratin-based teat sealant in distilled water

| Exm[1] | Time | Visual changes | Width | Ch-width[2] | Height | Ch_Height[3] |
|---|---|---|---|---|---|---|
| 1 | 16 hrs | Completely swollen and separated into many pieces of string-like material with some fractions floating | N/A[4] (25) | N/A | N/A (15) | N/A |
| 2 | 24 hrs | More material floating. Most of the test material on the bottom of the container | N/A (25) | N/A | N/A (14) | N/A |
| 3 | 40 hrs | Whole amount in small string and ball-like particles smaller than 10 mm | N/A (25) | N/A | N/A (13) | N/A |
| 4 | 48 hrs | NOC[5] | N/A (25) | N/A | N/A (17) | N/A |
| 5 | 64 hrs | | N/A (25) | N/A | N/A (19) | N/A |
| 6 | 72 hrs | NOC | N/A (25) | N/A | N/A (10) | N/A |

[1] Examination number;
[2] Change in the width from the previous observation (=previous observation − present observation);
[3] Change in the height from the previous observation (=previous observation − present observation);
[4] Test material not in one piece;
[5] No obvious changes

TABLE 4

Records for each observation for the keratin-based teat sealant in saline

| Exm[1] | Time | Visual changes | Width | Ch-width[2] | Height | Ch_Height[3] |
|---|---|---|---|---|---|---|
| 1 | 16 hrs | NOC[4] | 13 | 0 | 11 | 0 |
| 2 | 24 hrs | NOC | 13 | 0 | 10.5 | −0.5 |
| 3 | 40 hrs | NOC | 12 | −1 | 10 | 0 |
| 4 | 48 hrs | NOC | 12 | 0 | 10 | 0 |
| 5 | 64 hrs | NOC | 12 | 0 | 10.5 | 0.5 |
| 6 | 72 hrs | NOC | 12 | 0 | 10.5 | 0 |
| TOTAL | | | 13 | −1 | 11 | −0.5 |

[1]Examination number;
[2]Change in the width from the previous observation (=previous observation − present observation);
[3]Change in the height from the previous observation (=previous observation − present observation);
[4]No obvious changes Changes that occurred in the width or height of the test material in different media are shown in Table 5. There was some decrease in width or height in milk and saline and increase of the measures in distilled water. NB: measurements in distilled water are based as the form of the test material was defined by the container.

TABLE 5

Changes in width or height of the test item during the trial (in millimetres)

| Media | Width | Maximum change during trial | Difference | Height | Maximum change during trial | Difference |
|---|---|---|---|---|---|---|
| Milk | 8 | 6.5 | −1.5 | 10 | 11 | 1 |
| Distilled water | 16 | 25 | 9 | 12 | 19 | 7 |
| Saline | 13 | 12 | −1 | 11 | 10.5 | −0.5 |

Changes that occurred in the weight of the test material in different media are shown in Tables 6 and 7. There was a significant increase in the weight of the test material in all three media, with highest increase in distilled water.

TABLE 6

Changes in weight of keratin-based teat sealant in different media before and after the trial (in grams)

| Medium | A[1] | B[2] | C[3] | D[4] | E[5] |
|---|---|---|---|---|---|
| Milk | 7.8353 | 8.0492 | 19.682 | 9.0203 | 19.6491 |
| Distilled water | 7.8924 | 8.2042 | 19.0382 | 10.8617 | 19.0213 |
| Saline | 7.5993 | 7.862 | 19.7719 | 8.8325 | 19.723 |

[1]Weight of container only;
[2]Weight of container and keratin-based teat sealant (KBTS);
[3]Weight of container, KBTS, and fluid;
[4]End of trial weight of container and KBTS;
[5]End of trial weight of container, KBTS, and fluid

TABLE 7

Changes in test item weights in different media when compared at the beginning and ending of the trial (in grams)

| Medium | At trial start | At trial end | Weight gain | Percent |
|---|---|---|---|---|
| Milk | 0.2139 | 1.185 | 0.9711 | 454 |
| Distilled water | 0.3118 | 2.9693 | 2.6575 | 852.31 |
| Saline | 0.2627 | 1.2332 | 0.9705 | 369.43 |

Changes that occurred in the weight of the media during the trial are shown in Table 8. The weight of the media was decreased, with highest decrease in weight of the distilled water.

TABLE 8

Changes in weights of media when compared at the beginning and end of the trial (in grams)

| Medium | At trial start | At trial end | Weight loss | Percent |
|---|---|---|---|---|
| Milk | 11.6328 | 10.6288 | 1.004 | 8.63 |
| Distilled water | 10.834 | 8.1596 | 2.6744 | 24.69 |
| Saline | 11.9099 | 10.8905 | 1.0194 | 8.56 |

Discussion and Conclusion

Preliminary observations, in two different media (milk and tap water), when kept at domestic refrigerator temperatures showed apparent marked effects of osmolarity on the keratin-based teat sealant material. The present trail was conducted to quantify any changes in the weights and swelling of the keratin-based teat sealant when exposed to media with different osmolarity at room temperatures.

The findings of the preliminary observations (Example 2) and the present agree with observations that keratin appears to be highly susceptible to changes in the osmolarity of its environment. It is unlikely that a hypotonic environment will be present at the teat end at any time over the dry period. Thus, it is highly unlikely that the osmolarity will affect the physical characteristics of a keratin-based teat sealant, after application at last milking of the season.

During the present trial, the weights of the test material were significantly affected in different media, apparently associated with the hydrophilicity of the keratin in hypotonic media. Interestingly, in media with similar osmolarity, a higher weight gain occurred in milk than in saline but this would need to be further tested in a replicated design experiment to establish significance.

The surface of the material appeared to become more pasty in milk, suggesting that exposure to substances in milk may have partly disintegrated or adsorbed to the keratin-based teat sealant. Such exposure is likely to occur during the dry period, particularly during involution and colostrogenesis. It was hypothesized that the higher weight gain in milk than in saline occurred due to reaction with substances in milk.

The physical dimensions of the test material were also changed as demonstrated by height and width changes. Swelling in distilled water lead to changes in the integrity of the test material, where it became granular and broke into smaller pieces. In milk and saline, small changes in width and height were observed. It was postulated that these occurred due compaction of the material (increased density) or due to some dissolution in milk, possibly due to chemical reaction with substances in this medium.

It should be noted that, at observation 6, extraction of the test material from the milk was difficult because the milk had become yogurt-like, so the last measures in weight may be overestimates. In addition, during the squeezing phase it was found that the keratin-based teat sealant, exposed to air had dried in the nozzle and had become difficult to squeeze through the nozzle attachment. A further implication of the susceptibility to apparent hydration or dehydration is the potential for a change in the nature of the keratin when it is packed in syringes and stored under conditions of differing humidity, but this can be controlled by having capped treatment tubes.

From this, it was concluded that a batch of the product should be obtained to conduct a trial to check the irritability of the proposed treatment in a small number of cows before testing this proposed product in a field trial, as this product has not previously been put in the teats of cows.

Example 4

Determination of the Irritability and Acceptability of an Investigational Keratin-Based Intramammary Internal Teat Sealant Administered to Lactating Dairy Cattle The aim of this investigation included the goal of evaluating an intramammary keratin-based internal teat sealant formulation for irritability and acceptability of administration when 1 syringe per quarter was infused to lactating dairy cattle. The irritability of this product could only be tested by experimentation in cows. Dairy cattle at drying off are the target animal for the proposed use of the product. For initial irritability and acceptability tests, lactating cows were used. The study was designed for compliance with veterinary medicine standards.

Materials and Methods

Clinically healthy lactating cattle at the Number 1 dairy herd of Massey University were used. Cows that had been treated with antibiotic preparations within 30 days of study initiation or were debilitated, diseased or injured, fractious or otherwise unsuitable for inclusion were not used. The health of the udder was checked by palpation and a Rapid Mastitis Test. Animals with palpable abnormalities in any of the quarters or a positive RMT test (Trace or greater) on day −1 were not assigned to the study. Cow somatic cell information from the regular herd testing scheme was screened. Animals with counts>250,000 cell/ml at the test prior to the treatment day were not assigned to the study. Cows with the lowest SCC, negative RMT tests, four functional quarters, free of clinical signs of mastitis or teat abnormalities were assigned to the study.

Eight cows selected from Dairy No. 1, Agricultural Farm Services, Massey University, Palmerston North, with individual cow somatic cell counts of less than 100,000, negative on RMT check and with no palpable abnormalities in any of the udder quarters were assigned to the study. All cows assigned to the study were lactating animals with four functional quarters. Study animals were held at pasture and grazed as a single mob during the study. Cows were managed similarly and with due regard for their wellbeing.

The study included 6 treated and 2 untreated control cows that were allocated in an unbiased way using their ear tag number. Cows were ranked according to ascending ear tag number and were allocated to negative control (if positioned at rank 4 and 5) or the treatment group (for the rest of the enrolled cows). The experimental unit was a cow for SCC levels, but data was collected at the quarter level for residual product and clinical examination observations after treatment. Cows from the treatment group received a single treatment of investigational keratin-based internal teat sealant by intramammary infusion at an afternoon milking, whilst negative control cows were untreated.

Prior to application of treatments and starting with teats on the most distant part of the udder from the operator, teats were twice wiped with proprietary teat wipes (ethanol 70%, chlorhexidine 0.1%, and cetrimide 0.16%). Teat ends were visibly clean, being free of dirt or faecal contamination. Teats were allowed to dry completely prior to second wiping or applying the teat sealant. The nearest teats from the operator were treated first to minimise contamination. Treatment was administered using the partial insertion technique. After application all teats of both groups were sprayed with diluted iodine teat spray. A test batch of product manufactured by the supplier was used.

Examinations for detection of irritation were performed on all quarters by an experienced dairy technician. Individual quarters were observed and palpated for the presence of clinical signs indicative of irritation and mastitis, i.e., heat, swelling, a painful udder, or the presence of clots and flakes in the secretions. Each quarter was subjectively judged as irritated (change in score more than 2 score points over day or total score 4 and higher) or non-irritated according to the above criteria. Both udder and teat examinations were scored using the following parameters:

Clinical Assessment Scoring System:
1 No or virtually no stress, irritation, pain, erythema, or oedema.
2 Stress, irritation or pain of a minor intensity, or slight erythema or oedema (Well defined)
3 Stress, irritation or pain of a moderate intensity, or moderate erythema or oedema
4 Stress, irritation or pain of a severe intensity, or severe erythema (beet redness to slight eschar formation), or severe oedema (raised more than 1 mm and extending beyond the area of exposure)
5 Severe eschar and/or corrosion Scoring of the Amount of Product Retained at First Stripping after Treatment The amount of product retained and stripped out at the first milking post treatment was subjectively scored at a quarter level by palpation of the teats before stripping and visual examination of the material stripped out.

Product Retained Scoring System:
"−" None seen, teat does not feel like product inside
"+" Only 1-2 flecks seen, teat does not feel like product inside
"++" A few flecks, teat feels like small globule inside
"+++" A few strips of product, teat half full of product
"++++" Probably all amount stripped out, teat feel like completely full Cows had any residual keratin teat seal stripped-out the next morning and the amount of residual test item retrieved was scored. Cows were clinically assessed for signs of tissue irritation or mastitis at each milking for the first three days after treatment. Representative milk samples were collected from cows through "Westfalia" in-line sampling vessels that sample approximately 2% of the harvested milk throughout milking, in the ten days after treatment. The milk samples were representative at a cow level and were sub-sampled for testing of SCC and archiving. Samples for somatic cell counting were submitted to the Livestock Improvement Corporation (LIC) laboratory (Testlink) for SCC level determination on 6$^{th}$ Aug. 2007. ICSCC were determined using a Fossomatic cell counter. To calculate changes in SCC levels, mean values of the natural log+1 and their 95% confidence intervals were used.

Results

No circumstances were known to affect the quality or integrity of the study. No health problems or adverse events associated with the investigational treatment were observed. The treatment was acceptable to both the administrator and the test system, although the use of a small nozzle syringe somewhat reduced syringeability of the product. No visible or palpable clinical signs of inflammation or irritation were observed during the assessment period as indicated in Table 9.

Figure 2:
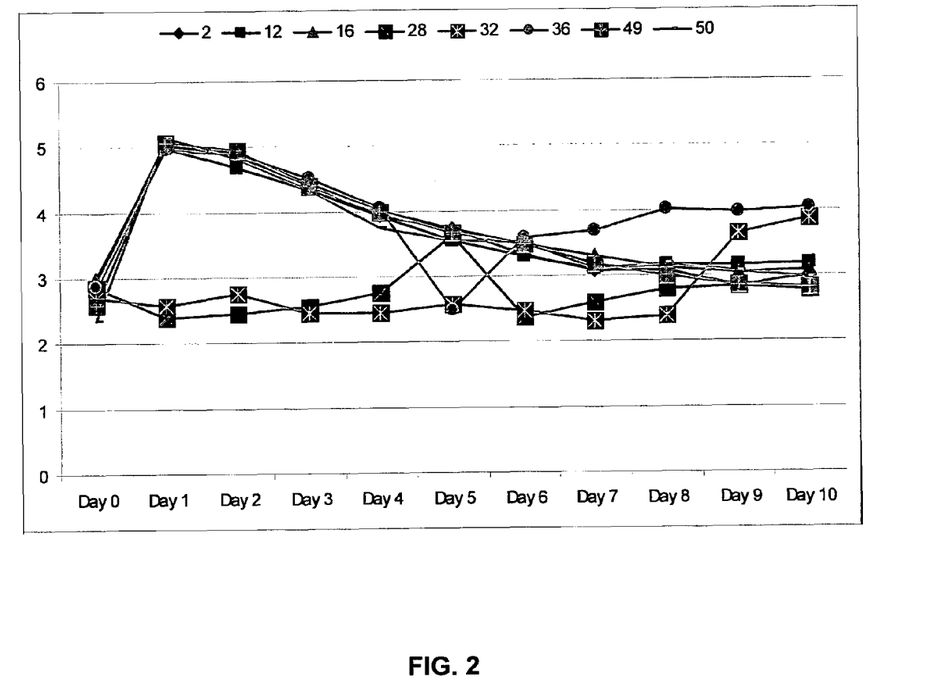
FIG. 2. The transformed (natural log+1) of individual cow somatic cell counts over the 10 day observation period described in Example 4. Cows 28 and 32 were untreated controls. All other cows were treated.

Somatic cell counts in the treated group, when compared to negative control group, were elevated for 3-4 days and reached the level of the negative control animals by day 9. The increase in somatic cells represents stimulation of the defence mechanisms of the udder. Keratin is a protein which appeared to cause a marked influx of polymorphonuclear cells of short duration into the milk in the treated mammary glands. A residual level of test item that approximated the amount inserted was retrieved from one cow with other stripping results as shown in Table 10. The rapidly and significantly increased levels of SCC indicated a transient immuno-stimulation reaction post treatment that returned to the ICSCC levels of untreated group by day 9 (see Table 11 and FIG. 2).

Conclusion

This trial has indicated no clinically discernable irritation resulting from the insertion of a keratin-based teat seal to lactating dairy cows. There was a response to the insertion of the keratin in terms of a sub-clinical inflammatory response that attracted leucocytes into the milk of the mammary gland. In view of its subclinical nature, spontaneous resolution and short duration such an outcome could assist in protecting the udder from infection in the first week of the dry period when it is most susceptible to bacterial infection. In view of the safety of the test product, the way now appears clear to further test the product in dairy cows at drying off, then to test the efficacy of the product in preventing mastitis in the dry period.

TABLE 9

Daily Clinical examination scores

| Cow Id | Date | FL | FR | RL | RR | FL (Diff) | FR (Diff) | RL (Diff) | RR (Diff) | Irritation |
|---|---|---|---|---|---|---|---|---|---|---|
| 2 | 26 Jul. 2007 | 1 | 1 | 1 | 1 | | | | | |
| 12 | 26 Jul. 2007 | 1 | 1 | 1 | 1 | | | | | |
| 16 | 26 Jul. 2007 | 1 | 1 | 2* | 2* | | | | | |
| 28 | 26 Jul. 2007 | 1 | 1 | 1 | 1 | | | | | |
| 32 | 26 Jul. 2007 | 1 | 1 | 1 | 1 | | | | | |
| 36 | 26 Jul. 2007 | 1 | 1 | 1 | 1 | | | | | |
| 49 | 26 Jul. 2007 | 1 | 1 | 1 | 1 | | | | | |
| 50 | 26 Jul. 2007 | 1 | 1 | 1 | 1 | | | | | |
| 2 | 27 Jul. 2007 | 1 | 1 | 1 | 1 | 0 | 0 | 0 | 0 | 0 |
| 12 | 27 Jul. 2007 | 1 | 1 | 1 | 1 | 0 | 0 | 0 | 0 | 0 |
| 16 | 27 Jul. 2007 | 1 | 1 | 2* | 2* | 0 | 0 | 0 | 0 | 0 |
| 28 | 27 Jul. 2007 | 1 | 1 | 1 | 1 | 0 | 0 | 0 | 0 | 0 |
| 32 | 27 Jul. 2007 | 1 | 1 | 1 | 1 | 0 | 0 | 0 | 0 | 0 |
| 36 | 27 Jul. 2007 | 1 | 1 | 1 | 1 | 0 | 0 | 0 | 0 | 0 |
| 49 | 27 Jul. 2007 | 1 | 1 | 1 | 1 | 0 | 0 | 0 | 0 | 0 |
| 50 | 27 Jul. 2007 | 1 | 1 | 1 | 1 | 0 | 0 | 0 | 0 | 0 |
| 2 | 28 Jul. 2007 | 1 | 1 | 1 | 1 | 0 | 0 | 0 | 0 | 0 |
| 12 | 28 Jul. 2007 | 1 | 1 | 2* | 1 | 0 | 0 | 1 | 0 | 0 |
| 16 | 28 Jul. 2007 | 1 | 1 | 1 | 1 | 0 | 0 | −1 | −1 | 0 |
| 28 | 28 Jul. 2007 | 1 | 1 | 1 | 1 | 0 | 0 | 0 | 0 | 0 |
| 32 | 28 Jul. 2007 | 1 | 1 | 1 | 1 | 0 | 0 | 0 | 0 | 0 |
| 36 | 28 Jul. 2007 | 1 | 1 | 1 | 1 | 0 | 0 | 0 | 0 | 0 |
| 49 | 28 Jul. 2007 | 1 | 1 | 1 | 1 | 0 | 0 | 0 | 0 | 0 |
| 50 | 28 Jul. 2007 | 1 | 2* | 1 | 1 | 0 | 1 | 0 | 0 | 0 |
| 2 | 29 Jul. 2007 | 1 | 1 | 1 | 1 | 0 | 0 | 0 | 0 | 0 |
| 12 | 29 Jul. 2007 | 1 | 1 | 2* | 1 | 0 | 0 | 0 | 0 | 0 |
| 16 | 29 Jul. 2007 | 1 | 1 | 1 | 1 | 0 | 0 | 0 | 0 | 0 |
| 28 | 29 Jul. 2007 | 1 | 1 | 1 | 1 | 0 | 0 | 0 | 0 | 0 |
| 32 | 29 Jul. 2007 | 1 | 1 | 1 | 1 | 0 | 0 | 0 | 0 | 0 |
| 36 | 29 Jul. 2007 | 1 | 1 | 1 | 1 | 0 | 0 | 0 | 0 | 0 |
| 49 | 29 Jul. 2007 | 1 | 1 | 1 | 1 | 0 | 0 | 0 | 0 | 0 |
| 50 | 29 Jul. 2007 | 1 | 1 | 1 | 1 | 0 | −1 | 0 | 0 | 0 |
| Sum | | 32 | 33 | 36 | 34 | | | | | |
| Average | | 1.000 | 1.031 | 1.125 | 1.063 | | | | | |

*On palpation this quarter was slightly firmer than the others, but clinically normal. It is likely that more residual milk was present. In the present scoring system a category to reflect this does not exist, and this quarter was wrongly scored as 2.

TABLE 10

Amount of product stripped out score

| Cow Id | Rx group | Date | FL | FR | RL | RR | Notes |
|---|---|---|---|---|---|---|---|
| 2 | 1 | 27 Jul. 2007 | ++ | ++ | + | + | |
| 12 | 1 | 27 Jul. 2007 | ++ | ++ | ++ | ++ | |
| 16 | 1 | 27 Jul. 2007 | + | +++ | − | ++ | |
| 28 | 2 | 27 Jul. 2007 | N/A | N/A | N/A | N/A | |

TABLE 10-continued

Amount of product stripped out score

| Cow Id | Rx group | Date | FL | FR | RL | RR | Notes |
|---|---|---|---|---|---|---|---|
| 32 | 2 | 27 Jul. 2007 | N/A | N/A | N/A | N/A | |
| 36 | 1 | 27 Jul. 2007 | +++ | ++++ | +++ | + | Had problem to milk out; re-strip and continue milking |
| 49 | 1 | 27 Jul. 2007 | + | ++ | + | − | |
| 50 | 1 | 27 Jul. 2007 | − | + | − | − | |

TABLE 11

ICSCC details

| | Date | | | | | | | |
|---|---|---|---|---|---|---|---|---|
| Cow Id | 26 Jul. 2007 Day 0 | 27 Jul. 2007 Day 1 | 28 Jul. 2007 Day 2 | 29 Jul. 2007 Day 3 | 30 Jul. 2007 Day 4 | 31 Jul. 2007 Day 5 | 1 Aug. 2007 Day 6 | 2 Aug. 2007 Day 7 |
| 2 | 85 | 11596 | 7425 | 2648 | 875 | 538 | 210 | 123 |
| 12 | 68 | 9615 | 4816 | 2166 | 859 | 354 | 198 | 125 |
| 16 | 100 | 10829 | 7945 | 2798 | 1041 | 540 | 313 | 206 |
| 28 | 71 | 25 | 28 | 35 | 57 | 416 | 24 | 39 |
| 32 | 50 | 38 | 58 | 29 | 29 | 37 | 30 | 20 |
| 36 | 77 | 9101 | 7824 | 3255 | 1120 | 31 | 390 | 491 |
| 49 | 40 | 11850 | 8704 | 2505 | 963 | 466 | 305 | 152 |
| 50 | 22 | 14060 | 6570 | 2206 | 556 | 359 | 330 | 126 |
| Average | 64.125 | 8389.25 | 5421.25 | 1955.25 | 687.5 | 342.625 | 225 | 160.25 |
| 95% CI | 17.58 | 3723.29 | 2435.56 | 856.22 | 298.74 | 140.72 | 95.08 | 101.35 |

| | Date | | | | | | |
|---|---|---|---|---|---|---|---|
| Cow Id | 3 Aug. 2007 Day 8 | 4 Aug. 2007 Day 9 | 5 Aug. 2007 Day 10 | Average | 95% CI | Upper | Lower |
| 2 | 120 | 70 | 100 | 2162.73 | 2260.45 | 4423.18 | −97.72 |
| 12 | 143 | 143 | 153 | 1694.55 | 1770.27 | 3464.82 | −75.73 |
| 16 | 134 | 110 | 118 | 2194 | 2186.07 | 4380.07 | 7.93 |
| 28 | 63 | 70 | 59 | 80.636 | 66.57 | 147.21 | 14.07 |
| 32 | 25 | 455 | 727 | 136.182 | 137.81 | 273.99 | −1.63 |
| 36 | 1015 | 957 | 1090 | 2304.64 | 1878.13 | 4182.77 | 426.51 |
| 49 | 101 | 73 | 67 | 2293.27 | 2406.96 | 4700.23 | −113.69 |
| 50 | 154 | 117 | 92 | 2235.65 | 2585.05 | 4820.69 | −349.41 |
| Average | 219.38 | 249.38 | 300.75 | | | | |
| 95% CI | 224.78 | 217.05 | 269.25 | | | | |

Where in the foregoing description reference has been made to integers or components having known equivalents, then such equivalents are incorporated as if individually set forth.

Although the invention has been described by way of example and with reference to possible embodiments, it is to be appreciated that improvements and/or modifications may be made without departing from the scope of the invention.

All publications and patents mentioned in the above specification are herein incorporated by reference.

The invention claimed is:

1. A method for reducing the incidence of mastitis in an animal including the step of: introducing a composition comprising a keratin paste into the teat canal of the animal, thereby reducing the incidence of mastitis in said animal.

2. The method according to claim 1 where the method is employed during the non-lactating period of the animal.

3. The method according to claim 2 where the animal is a cow.

4. The method according to claim 1 where the composition is in a form suitable for introduction by means of a syringe.

5. The method according to claim 4 where the composition has a viscosity of between $0.1 \times 10^6$ cP and $1.5 \times 10^6$ cP.

6. A method for inducing leucocytosis in the mammary gland of an animal including the step of: introducing a composition comprising a keratin paste into the teat canal of the animal, thereby inducing leucocytosis in said mammary gland of said animal.

7. The method according to claim 6 where the method is employed during the non-lactating period of the animal.

8. The method according to claim 6 where the animal is a cow.

9. The method according to claim 6 where the composition is in a form suitable for introduction by means of a syringe.

10. The method according to claim 9 where the composition has a viscosity of between $0.1 \times 10^6$ cP and $1.5 \times 10^6$ cP.

* * * * *